US00PP33638P2

(12) United States Plant Patent
Smutzer

(10) Patent No.: US PP33,638 P2
(45) Date of Patent: Nov. 16, 2021

(54) ***LEUCOPHYLLUM* PLANT NAMED 'GREHJS'**

(50) Latin Name: *Leucophyllum frutescens*
Varietal Denomination: GREHJS

(71) Applicant: Harry Joe Smutzer, El Campo, TX (US)

(72) Inventor: Harry Joe Smutzer, El Campo, TX (US)

(73) Assignee: Greenleaf Nursery Co., Park Hill, OK (US)

( * ) Notice: Subject to any disclaimer, the term of this patent is extended or adjusted under 35 U.S.C. 154(b) by 0 days.

(21) Appl. No.: 17/116,328

(22) Filed: Dec. 9, 2020

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. Anne Whealy

(57) ABSTRACT

A new and distinct cultivar of *Leucophyllum* plant named 'GREHJS', characterized by its upright to somewhat outwardly spreading plant habit; vigorous growth habit and rapid growth rate; freely branching habit; dense and bushy appearance; relatively large silver-colored leaves; freely flowering habit; relatively large reddish purple-colored flowers; relative resistant to pathogens; and good garden performance.

2 Drawing Sheets

Figure 1:
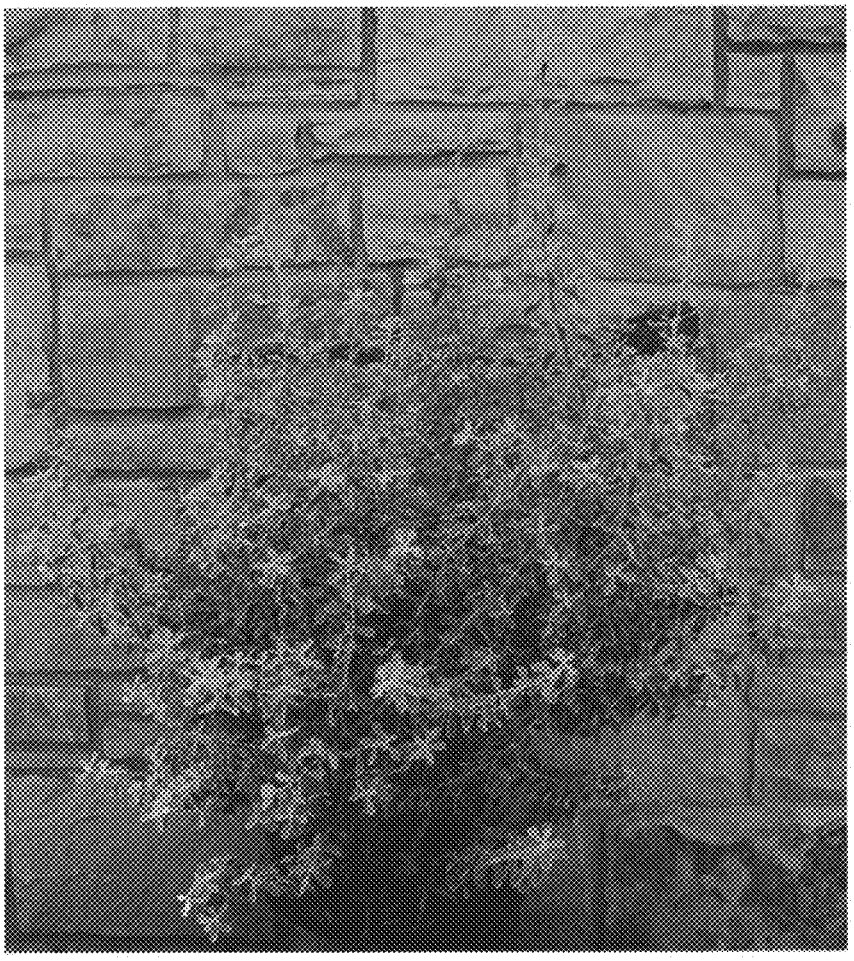
Figure 2:
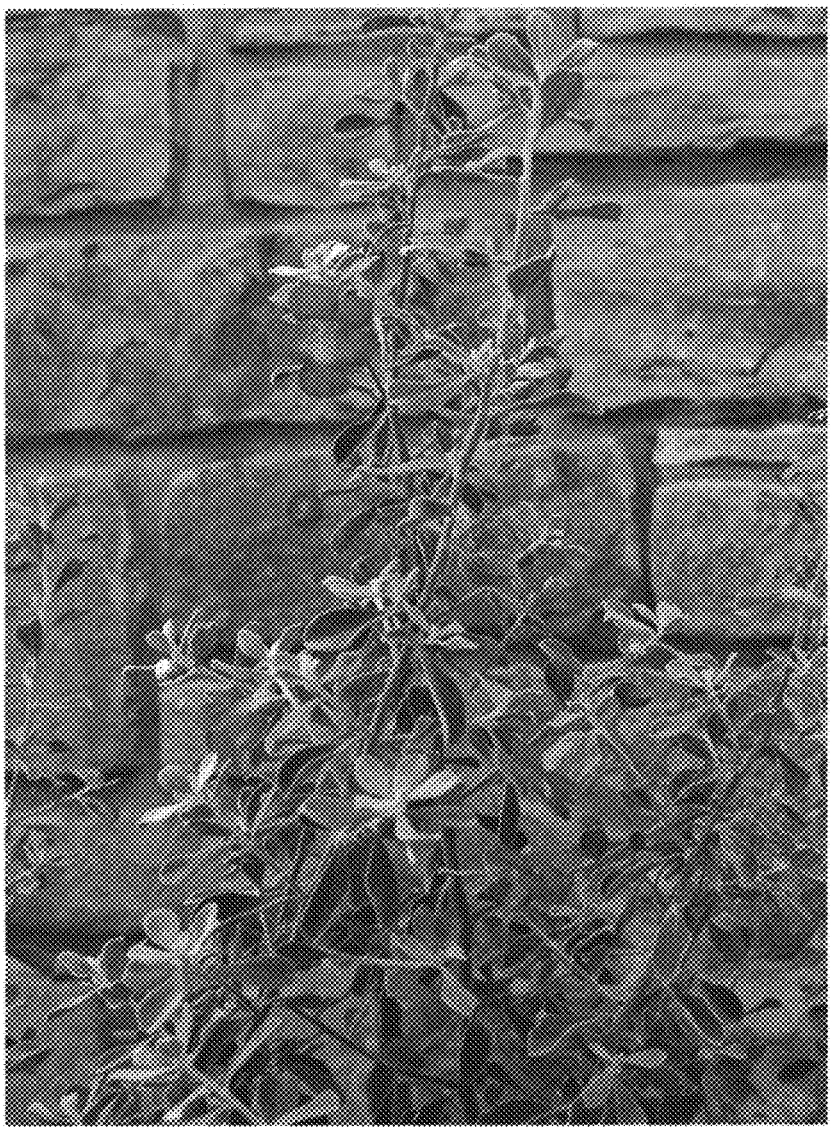

Botanical designation: *Leucophyllum frutescens.*
Cultivar denomination: 'GREHJS'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Leucophyllum* plant, botanically known as *Leucophyllum frutescens*, commonly referred to as Texas Sage and hereinafter referred to by the name 'GREHJS'.

The new *Leucophyllum* plant is a naturally-occurring whole plant mutation of *Leucophyllum frutescens* 'Greado', not patented. The new *Leucophyllum* plant was discovered and selected by the Inventor as a single plant from within a population of plants of 'Greado' in a controlled environment in El Campo, Tex. on Jun. 12, 2018.

Asexual reproduction of the new *Leucophyllum* plant by terminal vegetative cuttings in a controlled environment in El Campo, Tex. since Jul. 16, 2019, has shown that the unique features of this new *Leucophyllum* plant are stable and reproduced true to type in successive generations.

SUMMARY OF THE INVENTION

Plants of the new *Leucophyllum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'GREHJS'. These characteristics in combination distinguish 'GREHJS' as a new and distinct *Leucophyllum* plant:

1. Upright to somewhat outwardly spreading plant habit.
2. Vigorous growth habit and rapid growth rate.
3. Freely branching habit; dense and bushy appearance.
4. Relatively large silver-colored leaves.
5. Freely flowering habit.
6. Relatively large reddish purple-colored flowers.
7. Cuttings propagate easily with minimal loss.
8. Relatively resistant to pathogens common to *Leucophyllum* plants.
9. Good garden performance.

Plants of the new *Leucophyllum* differ primarily from plants of the mutation parent, 'Greado' in the following characteristics:

1. Plants of the new *Leucophyllum* are larger, more vigorous and grow faster than plants of 'Greado'.
2. Plants of the new *Leucophyllum* are more freely branching and denser than plants of 'Greado'.
3. Leaves of plants of the new *Leucophyllum* are larger and more silvery in color than leaves of plants of 'Greado'.
4. Flowers of plants of the new *Leucophyllum* are larger than flowers of plants of 'Greado'.

Plants of the new *Leucophyllum* can be compared to plants of *Leucophyllum frutescens* 'Silverado', not patented. In side-by-side comparisons, plants of the new *Leucophyllum* differ primarily from plants of 'Silverado' in the following characteristics:

1. Plants of the new *Leucophyllum* are larger, have longer internodes, are more vigorous and grow faster than plants of 'Silverado'.
2. Leaves of plants of the new *Leucophyllum* are larger and more silvery in color than leaves of plants of 'Silverado'.
3. Flowers of plants of the new *Leucophyllum* are larger than flowers of plants of 'Silverado', however plants of 'Silverado' are more freely-flowering than plants of the new *Leucophyllum*.
4. Plants of the new *Leucophyllum* are more resistant to pathogens common to *Leucophyllum* plants than plants of 'Silverado'.

BRIEF DESCRIPTION OF THE PHOTOGRAPHS

The accompanying colored photographs illustrate the overall appearance of the new *Leucophyllum* plant showing the colors as true as it is reasonably possible to obtain in colored reproductions of this type. Colors in the photographs may differ slightly from the color values cited in the detailed botanical description which accurately describe the colors of the new *Leucophyllum* plant. The photograph on the first sheet is a side perspective view of a typical flowering plant of 'GREHJS' grown in a container. The photograph on the second sheet is a close-up view of a typical flowering plant of 'GREHJS'.

DETAILED BOTANICAL DESCRIPTION

The aforementioned photographs and following observations and measurements describe plants grown during the spring and summer in containers in outdoor nurseries in El Campo and Fort Worth, Tex. and under cultural practices typical of commercial *Leucophyllum* production. Plants were one year from planting rooted young plants when the photographs and description were taken. In the following description, color references are made to The Royal Horticultural Society Colour Chart, 2015 Edition, except where general terms of ordinary dictionary significance are used.

Botanical classification: *Leucophyllum frutescens* 'GREHJS'.

Parentage: Naturally-occurring whole plant mutation of *Leucophyllum frutescens* 'Greado', not patented.

Propagation:

*Type.*—By terminal vegetative cuttings.

*Time to initiate roots, summer.*—About four to six weeks at minimum soil temperatures about 29° C.

*Time to produce a rooted young plant, summer.*—About ten to twelve weeks.

*Root description.*—Medium in thickness to thick, fibrous; typically white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Perennial shrub; upright to outwardly spreading plant habit; vigorous growth habit; rapid growth rate; freely branching habit with lateral branches potentially developing at every node; dense and bushy appearance.

*Plant height.*—About 77 cm.

*Plant diameter.*—About 81 cm.

Lateral branch description:

*Length.*—About 65 cm.

*Diameter, proximally.*—About 1.1 cm.

*Internode length.*—About 1.5 cm.

*Strength.*—Strong; flexible when developing.

*Aspect.*—Primary stems, mostly upright; lateral branches about 45° to 80° from primary stem axis.

*Texture and luster.*—Densely pubescent, lanate; matte; older stems, woody.

*Color, developing.*—Close to 143A; pubescence, close to 193A.

*Color, developed.*—Close to 199A; pubescence, close to 193A and 194A; when woody, close to 199A.

Leaf description:

*Arrangement.*—Alternate, simple.

*Length.*—About 3 cm.

*Width.*—About 1.5 cm.

*Shape.*—Obovate.

*Apex.*—Acute to obtuse.

*Base.*—Cuneate.

*Margin.*—Entire, not undulate.

*Texture and luster, upper and lower surfaces.*—Densely pubescent, lanate; matte.

*Venation pattern.*—Pinnate.

*Color.*—Developing leaves, upper surface: Close to 194A to 194B. Developing leaves, lower surface: Close to 194B. Fully expanded leaves, upper surface: Close to 194A; venation, close to 194A. Fully expanded leaves, lower surface: Close to 194A to 194B; midvein, close to 193A and lateral venation, close to 194A to 194B.

*Petioles.*—Length: About 2.5 mm. Diameter: About 2 mm. Strength: Strong, flexible. Texture and luster: Pubescent, lanate; matte. Color, upper and lower surfaces: Close to 193A.

Flower description:

*Flower arrangement and habit.*—Campanulate single flowers with six fused petals; flowers axillary; flowers face mostly outwardly to slightly nodding; freely flowering habit with single flowers potentially developing at every axil during the flowering season.

*Fragrance.*—Faint; sweet and pleasant.

*Natural flowering season.*—Plants flower continuously in the late summer and early autumn in Texas.

*Flower longevity.*—Flowers last about two to three days on the plant; flowers not persistent.

*Flower size.*—About 2.5 cm by 2.75 cm.

*Flower depth.*—About 2.5 cm.

*Flower throat diameter.*—About 1 cm.

*Flower tube length.*—About 2 cm.

*Flower tube diameter, proximally.*—About 3 mm.

*Flower buds.*—Length: About 1.1 cm. Diameter: About 6 mm. Shape: Obovate. Texture and luster: Petals, smooth, glabrous and matte; sepals, densely pubescent and matte. Color: Petals, close to N144A to N144B; sepals, close to 193A.

*Petals.*—Arrangement: Six fused petals in a single whorl; lower 66.7% of the petals are fused, upper 33.3% of the petals are free; petal lobes reflexing with development. Petal lobe length: About 1 cm. Petal lobe width: About 1 cm. Petal lobe shape: Rounded with broadly obtuse apex. Petal lobe margin: Entire; slightly undulate. Petal lobe texture and luster, upper surface: Pubescent; slightly glossy. Petal lobe texture and luster, lower surface: Smooth, glabrous with pubescence along the margins; slightly glossy. Throat and tube, texture and luster: Smooth, glabrous; slightly glossy. Color, petal lobes: When opening, upper surface: Close to 70B. When opening, lower surface: Close to 75A. Fully opened, upper surface: Close to 70B; venation, close to 70B; color does not change with development. Fully opened, lower surface: Close to 75B; venation, close to 75B; color does not change with development. Color, throat: Upper petals, close to 75A; lower petals, close to NN155D with spots, close to 163A to 163B; venation, similar to lamina colors. Color, tube: Upper petals, close to 75A; lower petals, close to NN155D with spots, close to 163A to 163B; venation, similar to lamina colors.

*Sepals.*—Arrangement: Tubular calyx with four to six sepals in a single whorl fused at the base. Calyx length: About 5 mm. Calyx diameter: About 4 mm. Sepal length: About 5 mm. Sepal width: About 1.5 mm. Shape: Lanceolate. Apex: Elongated acute. Margin: Entire. Texture and luster, upper surface: Smooth, glabrous with pubescence along the margins and midvein; slightly glossy. Texture and luster, lower surface: Densely pubescent; matte. Color, upper surface: Close to 144A. Color, lower surface: Close to 194A.

*Peduncles.*—Length: About 3 mm. Diameter: About 1 mm. Angle: About 45° from stein axis. Strength: Strong, flexible. Texture and luster: Densely pubescent; matte. Color: Close to 193A.

*Reproductive organs.*—Stamens: Quantity: Four per flower. Filament length: About 1 cm. Filament color: Close to NN155D. Anther size: About 2 mm by 1 mm. Anther shape: Oblong, curled. Anther color: Close to 158A. Pollen amount: None observed. Pistils: Quantity: One per flower. Pistil length: About 1.3 cm. Style length: About 1.1 cm. Style color: Close to NN155D. Stigma diameter: About 1 mm. Stigma shape: Rounded. Stigma color: Close to NN155D. Ovary color: Close to 144B.

*Seeds and fruits.*—To date, seed and fruit development have not been observed on plants of the new *Leucophyllum.*

Pathogen resistance: Plants of the new *Leucophyllum* have been observed to be relatively resistant to pathogens common to *Leucanthemum* plants.

Garden performance: Plants of the new*Leucophyllum* have been observed to have good garden performance and to suitable for USDA Hardiness Zone 8.

It is claimed:

1. A new and distinct *Leucophyllum* plant named 'GREHJS' as illustrated and described.

* * * * *